US012290630B2

(12) United States Patent
Eggimann (10) Patent No.: US 12,290,630 B2
(45) Date of Patent: May 6, 2025

(54) INHALER JACKET WITH CAP ATTACHMENT

(71) Applicant: JAGOTEC AG, Muttenz (CH)

(72) Inventor: Thomas Eggimann, Muttenz (CH)

(73) Assignee: JAGOTEC AG, Muttenz (CH)

( * ) Notice: Subject to any disclaimer, the term of this patent is extended or adjusted under 35 U.S.C. 154(b) by 712 days.

(21) Appl. No.: 17/292,763

(22) PCT Filed: Nov. 12, 2019

(86) PCT No.: PCT/EP2019/081041
§ 371 (c)(1),
(2) Date: May 11, 2021

(87) PCT Pub. No.: WO2020/120052
PCT Pub. Date: Jun. 18, 2020

(65) Prior Publication Data
US 2021/0393895 A1    Dec. 23, 2021

(30) Foreign Application Priority Data
Nov. 12, 2018 (EP) ..................................... 18205755

(51) Int. Cl.
*A61M 15/00* (2006.01)
(52) U.S. Cl.
CPC . *A61M 15/0026* (2014.02); *A61M 2205/0216* (2013.01)
(58) Field of Classification Search
CPC ...... A61M 15/0026; A61M 2205/0216; A61M 2209/00; A61M 15/009; B65D 55/16
See application file for complete search history.

(56) References Cited

U.S. PATENT DOCUMENTS

| | | | |
|---|---|---|---|
| 5,200,153 A * | 4/1993 | Carr | B01L 3/50825 422/550 |
| 5,899,200 A * | 5/1999 | McNary | B65D 83/40 128/200.14 |
| 6,397,837 B1 * | 6/2002 | Ferris | A61M 15/009 128/200.14 |

(Continued)

FOREIGN PATENT DOCUMENTS

| WO | WO 2014/052263 A1 | 4/2014 |
|---|---|---|
| WO | WO 2014/147550 A1 | 9/2014 |
| WO | WO 2017/141194 A1 | 8/2017 |

OTHER PUBLICATIONS

International Search Report for International Application No. PCT/EP2019/081041, Jan. 23, 2020.

(Continued)

*Primary Examiner* — Justine R Yu
*Assistant Examiner* — Matthew R Moon
(74) *Attorney, Agent, or Firm* — FINNEGAN, HENDERSON, FARABOW, GARRETT & DUNNER, LLP (57) ABSTRACT

The invention discloses an accessory for an inhalation device having a canister and a housing including a mouthpiece from which the medicament is dispensed. The accessory includes a jacket, which attaches to the housing; a cap for the mouthpiece and a plurality of elastomeric straps which secure the jacket to the cap. An inhalation device is also provided with the accessory attached.

13 Claims, 7 Drawing Sheets

(56) References Cited

U.S. PATENT DOCUMENTS

| | | | | |
|---|---|---|---|---|
| 7,073,679 B1* | 7/2006 | Lagler | ............... | B65D 55/16 |
| | | | | 220/837 |
| 7,082,493 B1* | 7/2006 | Bhugra | ............. | G11C 15/00 |
| | | | | 711/108 |
| 7,082,943 B1 | 8/2006 | Clark | | |
| 7,131,441 B1* | 11/2006 | Keller | ............... | G06M 1/22 |
| | | | | 128/203.23 |
| 8,397,714 B2* | 3/2013 | Pearson | ......... | A61M 15/0096 |
| | | | | 128/200.14 |
| 2004/0089292 A1* | 5/2004 | Pollet | ............ | A61M 15/009 |
| | | | | 222/402.1 |
| 2004/0179971 A1* | 9/2004 | Ferguson | ............ | B01L 9/06 |
| | | | | 422/400 |
| 2006/0032495 A1* | 2/2006 | Fernandez | .......... | A45F 5/00 |
| | | | | 128/200.23 |
| 2007/0074718 A1* | 4/2007 | Austin | .......... | A61M 15/0086 |
| | | | | 128/200.23 |
| 2016/0051776 A1* | 2/2016 | Von Hollen | ...... | A61M 15/009 |
| | | | | 128/203.14 |

OTHER PUBLICATIONS

Written Opinion of the International Searching Authority for International Application No. PCT/EP2019/081041.

* cited by examiner

INHALER JACKET WITH CAP ATTACHMENT

This application is a national stage filing under 35 U.S.C. § 371 of International Application No. PCT/EP2019/081041, filed on Nov. 12, 2019, which claims priority to European Patent Application No. 18205755.4, filed Nov. 12, 2018. The contents of these applications are each incorporated herein by reference.

INTRODUCTION

The use of medicament inhalers for the treatment of respiratory diseases such as asthma and chronic obstructive pulmonary disease (COPD) is well known.

One type of medicament inhaler that is commonly used by both adults and children is the pressurized metered dose inhaler (pMDI). Such inhalers typically comprise a canister and an actuator.

The canister comprises an open-ended container normally made from metal such as aluminium that is sealingly capped by a metering valve assembly and filled with a pressurised medicament aerosol formulation. The formulation is stored either as a solution or as a suspension and comprises one or more drugs and a liquefied propellant, and optionally one or more excipients and/or adjuvants.

The actuator comprises a generally L-shaped hollow tubular construction, which has a first open end adapted to receive the canister, referred to as the actuator housing, and a second open end, which acts as a mouthpiece. The actuator is typically formed from a plastics material such as polypropylene or high-density polyethylene (HDPE).

After shaking the device, the user self-administers the aerosol medicament from the pMDI by applying a force on the canister to push it into the actuator housing thereby opening the valved outlet and causing the pre-metered aerosol medicament to be conveyed from the valved outlet through the actuator housing and discharged from the mouthpiece. Upon discharge from the canister, the medicament is "atomised" forming an aerosol. Simultaneously with this action, the user inhales through the mouthpiece, entraining the aerosol in the inhaled stream of air. The user then releases the force applied to the canister and the canister is returned to its resting position. The metering valve of the valve is re-charged and the following dose is metered.

When not in use, the inhaler mouthpiece is generally protected with a removable cap, which prevents dirt and dust particles from entering the actuator housing. If the mouthpiece is left uncovered, these particles may accumulate in the actuator housing and interfere with medicament dispensing or be inhaled by the user potentially causing severe pulmonary irritation. These caps however, due to their size, are easily lost by the user and can also be considered a choking hazard if accidentally swallowed by young children. Consequently it has become desirable for caps to be directly or indirectly attached by some means to the actuator housing.

BACKGROUND TO THE INVENTION

Direct Attachment

WO199612661 discloses a dispensing apparatus where a cap is attached to the housing by a strap formed of a web of plastics material with transverse grooves defining fold lines about which the web is foldable in bellows. Here the cap, strap and housing are either formed unitarily from a plastics material and the strap extends tangentially to the side of the housing or the strap is secured to the housing by means of co-operating stud fastener formations.

WO200204056 discloses an inhaler in which the cap is connected to the housing by a strap formed of a thermoplastic elastomer material. The strap is joined to the cap and housing by mechanical fasteners, glue, heated or ultrasonic welds or a combination of these means. The cap is attached via the strap to the side or end wall of the housing. The mouthpiece and the cap are also provided with co-operating snap-fit connectors.

WO2005046774 discloses an inhaler in which the cap is attached to the actuator body by means of an integrated strap, which underlies the base of the body and can pivot relative to the body. The cap is arranged to slide on the strap, such that the cap must translate away from the mouthpiece prior to the pivoting of the strap.

WO2005087299 discloses an inhaler in which the cap is attached to the housing by means of a telescopic strap. The telescopic strap is double hinged and consists of two components; a first component is attached to the cap by a hinge, e.g. a "living hinge", and the second component is attached to the housing in the same way but optionally also with a hole that fits over a stud on the housing.

Indirect Attachment

U.S. Pat. No. 7,082,943 discloses a fabric inhaler cover with a tubular main portion to substantially enclose the inhaler body and a fabric cap hood. The hood is sized to receive and retain the inhaler cap which is tethered to one side of the main portion. The cover can also accommodate a carry strap.

WO2014147550 discloses a usage event monitoring device that may be removably coupled to a medicament delivery device via a housing. The usage event monitoring device includes a tether that may take any shape, be formed from any material and reside in any location. Furthermore the tether can be removably coupled to a cap holder or directly attached to a cap.

US20150246187 discloses a dispensing assembly wherein the cap is removably attached to the actuator housing with an adhesive tape having one portion affixed to the housing and a second portion affixed to the cap.

WO2015030610 discloses a compliance monitor that can be housed within a second housing being releasably attached to the medicament inhaler. The second housing can be adapted to partially or fully enclose the medicament inhaler. Also the cap can be attached to the second housing by a tether.

There are however problems associated with the aforementioned prior art. Caps generally engage with the mouthpiece by way of varying click fit arrangements (i.e. projections in a co-operating relationship with grooves) which require the user to pinch or pull the cap from the top, bottom or sides with some force. This complicates cap removal especially for the young and elderly such that the user may decide to stop using the cap altogether leaving the mouthpiece uncovered between actuations.

A problem encountered with inhaler straps made from rigid plastic that only flex at fold lines is that these straps are more susceptible to breakage since continual folding during use weakens the fold lines. Inappropriate twisting of the strap either by the user or through poor inhaler storage (e.g. cold temperatures) may also cause the strap to break.

A problem with using a single elastic strap to attach the cap to the actuator housing is that when the cap is disengaged from the mouthpiece it can twist and provides no real alignment with the mouthpiece, which for visually impaired individuals could hinder cap re-attachment. Furthermore, using a single strap increases the risk of the cap being accidentally dislodged from the mouthpiece should the strap catch on an object.

Another problem with devices known in the art is that when straps are tethered to the base of the actuator housing, the user will be subjected to an additional user step since the thumb cannot be correctly positioned at the base of the actuator until the inhaler cap has been removed. This may inconvenience the user if immediate relief is required or if the user suffers from arthritis.

A problem with a fabric inhaler cover is that it will obscure all inhaler indentations and protrusions making the inhaler difficult to hold and operate. Furthermore, the fabric will easily mark from regular handling and may also obscure the dose counter. There is also the possibility that fabric fibers may enter the inhaler housing and become inhaled by the user.

A problem associated with a housing being releasably attached to the actuator is that the user may inadvertently loose the housing or forget to re-attach.

A problem with using adhesive tape to attach a cap to the actuator housing is that adhesive tape preferably adheres to smooth surfaces. Rough or irregular surface features on the cap or actuator housing (e.g. grip dimples or ridges) may prevent proper adherence, thereby impacting attachment. Furthermore, it is known that standard glues do not stick sufficiently well to Poly-olefins like PP, PE and HDPE. The glue is also sensitive to humidity and will start to loose its adhesive properties if stored inadequately.

It is therefore desirable to provide a means of attaching a cap to an actuator housing that is inexpensive (i.e. without requiring any modifications to the tooling used to produce the actuator housing), durable and does not suffer from the drawbacks discussed in the prior art.

BRIEF DESCRIPTION OF THE INVENTION

The present invention improves upon previous inhaler cap attachment means by providing an inhaler accessory that directly attaches to an inhaler housing. Thus, in a first aspect, the present invention provides an accessory for an inhaler, the accessory comprising:
(a) a jacket which attaches to a housing;
(b) a cap for a mouthpiece;
(c) and a plurality of elastomeric straps which connect the jacket to the cap;
wherein one end of each strap is secured to the jacket and the other end of each strap is secured to the cap.

In a second aspect of the present invention there is provided an inhaler for dispensing doses of medicament, the inhaler comprising:
(a) an actuator housing including a mouthpiece from which the medicament is dispensed
(b) and an inhaler accessory comprising:
 a jacket which attaches to the housing;
 a cap for the mouthpiece;
 and a plurality of elastomeric straps which connect the jacket to the cap;
wherein one end of each strap is secured to the jacket and the other end of each strap is secured to the cap.

DETAILED DESCRIPTION OF THE INVENTION

Jacket

In one embodiment a jacket is provided comprising an upper collar portion; a lower base portion and a pair of side walls. In one embodiment the side walls extend vertically between and connect to the upper collar portion and the lower base portion. The side walls improve the bending strength of the jacket thereby facilitating the process of inhaler attachment. The side walls may also function as structural supports. In one embodiment the lower base portion has a semi-circular configuration which ensures that the thumb recess on the inhaler actuator base is not obscured and is still usable. Furthermore, the lower base portion may function as an inhaler stand, holding the inhaler in a more favoured upright position when not in use.

In one embodiment the jacket is configured to receive and attach to the inhaler actuator housing. In one embodiment the jacket is permanently attached to the housing. Attachment may be mechanical, chemical or by a combination of these means. In one embodiment attachment is by a mechanical means.

In one embodiment mechanical attachment may comprise at least one snap-fit fixing. In one embodiment attachment may comprise a plurality of snap-fit fixings which may be positioned around the top and/or bottom of the jacket such that upon receiving the inhaler, the snap-fit fixings engage and permanently lock the actuator housing in place. In a further embodiment, the snap-fit fixings are tamper-resistant and any attempt to remove the inhaler would destroy the snap-fit fixings preventing jacket re-attachment.

Alternatively, mechanical attachment comprises at least one clip fixing. In an alternative embodiment attachment may comprise a plurality of clip fixings which may be positioned around the top and/or bottom of the jacket such that upon receiving the inhaler, the clip fixings engage and permanently lock the actuator housing in place. In a further embodiment, the clip fixings are tamper-resistant and any attempt to remove the inhaler would destroy the clip fixings preventing jacket re-attachment.

In one embodiment the jacket only partially encloses the inhaler housing. In one embodiment the front and rear of the jacket are substantially open. These openings ensure that forward or rear facing actuator dose counters are not obscured when the jacket is attached.

In one embodiment the jacket is made from a resilient, substantially rigid material, more preferably a rigid plastics material such as polypropylene, high-density polyethylene (HDPE) or poly-acrylonitrile-butadiene-styrene or combinations thereof. Other medical grade rigid plastics material may also be used. In one embodiment the jacket is moulded in one piece, for example by injection moulding.

The thickness of the jacket wall will depend on the choice of plastics material selected; the force required to attach the jacket to the housing and the pull required to remove the cap from the mouthpiece once the jacket is in the attached position. In one embodiment the thickness of the jacket wall is from 0.05 mm to 1.5 mm in width for example from 0.1 mm to 1.0 mm in width or from 0.15 mm to 0.5 mm in width. In one embodiment the jacket wall will have varying dimensions of wall thicknesses. In one embodiment the jacket wall will have varying dimensions of wall thicknesses such that the thinnest region on the jacket wall is from 0.05 mm to 1.15 mm in width and the thickest region on the jacket wall is from 0.5 mm to 1.5 mm in width.

In one embodiment the jacket is moulded from different colours of plastics material for the purpose of distinguishing one jacket from another. For example, jacket colour may be used to identify medication type and/or dose used. It may therefore be desirable to match the colour of the jacket with that of the housing/and or cap. Alternatively the jacket is moulded from transparent plastics to ensure that when the jacket is attached to the housing, the housing colour is still clearly visible. In a further embodiment of the invention the jacket, whether moulded from coloured or transparent plastics material, may also be impregnated with glow-in-the-dark phosphorescent material to assist inhaler location in the dark. Alternatively, the jacket may be moulded from coloured or transparent phosphorescent plastics material.

In one embodiment the jacket is provided with an external textured surface. In one embodiment coverage may be full or partial. In one embodiment the jacket surface is provided with ridges, raised protrusions and/or indentations, which serve to improve the users grip during use.

In another embodiment the jacket is provided with an integrally moulded eyelet. In one embodiment the eyelet is located near to the top of the jacket for example on the outer surface of the upper collar. The eyelet may be used to attach the jacket to a key ring, a lanyard or to an extendable/retractable tether to provide the user with a carrying means while for example exercising.

Straps

In one embodiment the inhaler housing is attached to a cap by a plurality of straps. In one embodiment the inhaler housing is attached to a removable and replaceable cap for a mouthpiece by a plurality of straps. In one embodiment the inhaler housing is attached to a cap by a pair of straps. In one embodiment the inhaler housing is attached to a cap by a pair of straps diametrically opposing one another. In one embodiment the inhaler housing is attached to a cap by an opposing pair of parallel straps.

In an alternative embodiment the jacket is attached to a cap by a plurality of straps. In one embodiment the jacket is attached to a removable and replaceable cap for a mouthpiece by a plurality of straps. In one embodiment the jacket is attached to a cap by a pair of straps. In one embodiment the jacket is attached to a cap by a pair of straps diametrically opposing one another. In one embodiment the jacket is attached to a cap by an opposing pair of parallel straps.

In one embodiment the jacket is attached to the cap by straps made from flexible material such as an elastic material. In one embodiment the flexible material is a thermoplastic elastomer (TPE) such as Santoprene®, Pebax®, Vitaprene® or Hytrel®. Alternatively, the flexible material is a liquid silicone rubber (LSR) such as Elastosil®, Silpuran® or Silopren®. In one embodiment the choice of material selected provides the strap with an elongation means of at least 20%, at least 30%, at least 40%, at least 50%, at least 60% or at least 70% when compared to the original length of the strap.

In one embodiment each strap is pivotally secured to a jacket side wall. In one embodiment one end of each strap is pivotally secured to the jacket side wall and the other end of each strap is immovably secured to a corresponding cap side wall. In one embodiment one end of each strap is pivotally secured to a lower end of the jacket side wall and the other end of each strap is immovably secured to a cap side wall. In one embodiment one end of each strap is pivotally secured to a lower end of the jacket side wall and the other end of each strap is immovably secured to a corresponding cap side wall. In one embodiment one end of each strap is pivotally secured to a lower end of the jacket side wall by a pivot hinge. The inhaler accessory is therefore provided with two pivot hinges. Having two pivot hinges positioned parallel to one another provides the user with better cap control and mouthpiece alignment and also lessens the risk of strap twisting. In one embodiment the strap end which is pivotally secured to the lower end of the jacket side wall is provided with an engaging pivot member, which may be integrally moulded thereon. In one embodiment the engaging pivot member is a pin, a bolt, an axle or a stud. In one embodiment the engaging pivot member is a pivot pin with a flat circular head portion and a circular or oval rod portion. In one embodiment the pivot pin consists of a flat, enlarged, circular head portion and a circular or oval rod portion.

In one embodiment the lower end of each jacket side wall is provided with an aperture for receiving and securing one end of each strap, i.e. the engaging pivot member. In one embodiment the aperture is located on a raised portion of the lower end of the jacket side wall. In one embodiment the aperture is located on a flange for example a semi-circular flange which extends beyond the lower end of the jacket side wall. In one embodiment the aperture has a circular or non-circular shaped configuration. In one embodiment the aperture is a key-hole shaped slot.

In one embodiment, each strap is integrally moulded with a pivot pin having a flat circular head portion and an oval rod portion and engages with a key-hole shaped aperture positioned on a raised section of the lower jacket side wall. In one embodiment the neck diameter of the key-hole shaped slot is smaller than the diameter of the oval shaped rod portion. Furthermore, the diameter of the flat circular head portion of the pivot pin is larger than the diameter of the circular section of the key-hole shaped slot. This arrangement ensures that the strap can be securely attached to the jacket but remains freely rotatable. Due to the flexible nature of the strap, the pivot hinge is assembled by inserting the pivot pin into the tapered end of the key-hole shaped slot. In one embodiment transfer of the hinge pin to the circular section of the key-hole shaped slot requires the oval rod portion to undergo temporary deformation.

In an alternative embodiment, each strap is integrally moulded with a pivot pin having a flat circular head portion and a circular rod portion and engages with a circular shaped aperture located on a semi-circular flange extending beyond the lower end of the jacket side wall. In one embodiment the diameter of the circular aperture is smaller than the diameter of the flat circular pin head but larger than the diameter of the circular rod portion. This arrangement ensures that the strap is securely attached to the jacket but remains freely rotatable. Due to the flexible nature of the strap, the pivot hinge is assembled by physically inserting the pivot pin through the circular shaped receiving aperture.

Alternatively the jacket and straps are manufactured by a co-moulding process such that the hinge pin is moulded directly within the circular shaped receiving aperture.

In one embodiment each strap also comprises a central expansion region which is flanked on one side by the end region that is pivotally secured to a lower end of the jacket side wall and on the other side by the end region that is immovably secured to a cap side wall. In one embodiment the strap tapers at the central expansion region. In one embodiment the central expansion region is provided with a plurality of spaced apertures. In another embodiment the apertures are substantially circular or rectangular. In an alternative embodiment the central expansion region is provided with a plurality of alternating top and bottom cuts extending in a vertical plane or in a diagonal plane. In one embodiment the cuts are in a diagonal plane. Such structural features are believed to provide the central expansion region with improved means of elongation. In one embodiment the central expansion region provides the strap with at least a 50% or between a 50% to 100% improvement in strap elongation when compared to the original length of the strap. In one embodiment at least 60%, at least 70%, at least 80% or at least a 90% improvement in strap elongation is provided when compared to the original length of the strap. Note that elongation or stretch are used interchangeably herein since elasticity is described as the ability of a material to elongate or stretch when tension is applied, and to recover to its original shape when the tension is released.

Without wishing to be bound by theory, it is believed that it is both the choice of material selected from which the strap is manufactured as well as the structural features used in the central expansion region that influence total % strap elongation before permanent deformation or breakage. In one embodiment total % strap elongation (ε Total) is calculated as the sum of the elongation properties (%) provided by the material (ε Material) and the improved elongation means (%) provided by the design features in the central expansion region (ε Design). The equation for the total % of strap elongation is therefore provided as:

$$\varepsilon\text{Total} = \varepsilon\text{Material} + \varepsilon\text{Design}$$

In one embodiment total % strap elongation is at least 50%, at least 60%, at least 70%, at least 80%, at least 90%, at least 100%, at least 110%, at least 120%, at least 130%, at least 140% or at least 150% when compared to the original length of the strap.

Cap

In one embodiment the cap is a removable and replaceable cap for an inhaler mouthpiece. In one embodiment the cap of the present invention has a tubular portion, with a closed end and an open end. In one embodiment the tubular portion, which includes a top, a bottom and side surfaces is sized to slide over the mouthpiece. In one embodiment the cap is made from the same plastics material as the jacket. In an alternative embodiment the cap is made from the same plastics material as the straps. In one embodiment the cap is attached to the jacket by a pair of straps that are immovably secured to the cap.

In one embodiment the straps and cap are made from a thermoplastic elastomer or a liquid silicon rubber or a combination thereof. In one embodiment the cap and straps are moulded as one piece, for example by injection moulding.

In an alternative embodiment the straps are immovably attached to the cap by a co-moulding process. In one embodiment the process is a two-step co-moulding process. In one embodiment the process includes a first moulding step in which the cap is made from a rigid plastics material such as polypropylene, high-density polyethylene (HDPE) or poly-acrylonitrile-butadiene-styrene or combinations thereof and a second moulding step where the thermoplastic elastomer or liquid silicon rubber straps are moulded intimately with the cap. In one embodiment the cap is moulded in the first moulding step with a plurality of voids on the cap side walls to accept the thermoplastic elastomer or liquid silicon rubber. In one embodiment the straps are immovably secured to the cap through a combination of mechanical (e.g. mechanical anchoring) and physical (e.g. fusion during the moulding process) means. Furthermore, the presence of the strap ends on the cap side walls may provide the user with additional gripping means.

In one embodiment each strap is partially stretched by less than 10%, less than 9%, less than 8%, less than 7%, less than 6%, less than 5%, less than 4%, less than 3% less than 2% or less than 1% when the cap is engaged with the mouthpiece when compared to the original length of the strap. In one embodiment each strap is partially stretched by 0.01% to 9%, 0.1% to 7%, 0.5% to 5% or by 1% to 3% when the cap is engaged with the mouthpiece when compared to the original length of the strap.

In one embodiment of the present invention there is provided an accessory for an inhaler, the accessory comprising:
(a) a jacket which attaches to a housing;
(b) a removable and replaceable cap for a mouthpiece;
(c) and a plurality of elastomeric straps which connect the jacket to the cap;

wherein one end of each strap is pivotally secured to a jacket side wall and the other end of each strap is immovably secured to a corresponding cap side wall, and wherein each strap is partially stretched by less than 10% when the cap is engaged with the mouthpiece.

In another embodiment of the present invention there is provided an inhaler for dispensing doses of medicament, the inhaler comprising:
(a) an actuator housing including a mouthpiece from which the medicament is dispensed
(b) and an inhaler accessory comprising:
a jacket which attaches to the housing;
a cap for the mouthpiece;
and a plurality of elastomeric straps which connect the jacket to the cap;

wherein one end of each strap is secured to the jacket and the other end of each strap is secured to the cap.

In one embodiment each strap is secured to the corresponding jacket and cap side wall. In one embodiment the strap end which is pivotally secured to the jacket side wall is pivotally secured to a lower end of the jacket side wall. In one embodiment the jacket is attached to the cap by a pair of elastomeric straps.

The jacket can be sized to fit around the housing of any inhalation device. In one embodiment the inhaler is a dry powder inhaler, a pressurized metered dose inhaler or a nebulizer. In one embodiment the inhaler dispenses doses of medicament from a canister.

In one embodiment the cap is movable between first, second and third positions and remains attached to the jacket at each position; in a first position the cap is arranged to engage with the mouthpiece; in a second position the cap is drawn laterally outwards away from the mouthpiece and in a third position the cap is rotated in an anti-clockwise direction fully exposing the mouthpiece for use.

In one embodiment the cap rotates by at least 70 degrees about a horizontal axis of rotation. In one embodiment the cap rotates by at least 80 degrees, by at least 90 degrees or by at least 100 degrees about a horizontal axis of rotation.

In one embodiment the straps in a first position (also referred to as the closed position) are partially stretched or elongated and here the cap engages with the mouthpiece. In one embodiment the straps are partially stretched when the cap is engaged with the mouthpiece. In one embodiment each strap is partially stretched by less than 10%, less than 9%, less than 8%, less than 7%, less than 6%, less than 5%, less than 4%, less than 3%, less than 2% or less than 1% when compared to the original length of the strap. Advantageously as the straps in the first or closed position are partially stretched, the cap and mouthpiece no longer require co-operating snap-fit fixings. Furthermore having the straps partially stretched when the cap is engaged with the mouthpiece also minimises the risk of the straps catching on an object, which could accidentally dislodge the cap.

In one embodiment the straps in a second position are stretched or fully stretched and the cap is drawn laterally outwards away from the mouthpiece. In one embodiment each strap is stretched or fully stretched by at least 50%, at least 60%, at least 70%, at least 80%, at least 90%, at least 100%, at least 110%, at least 120%, at least 130%, at least 140% or at least 150% when compared to the original length of the strap.

In one embodiment the straps in a third position are unstretched and here the cap will have been rotated in an anti-clockwise direction fully exposing the mouthpiece ready for use. In one embodiment the cap will have rotated by at least 70 degrees about a horizontal axis of rotation.

In one embodiment the cap is movable between first, second and third positions and remains attached to the jacket in each position; in a first position the straps are partially stretched and ensure that the cap is engaged with the mouthpiece; in a second position the straps are stretched and the cap is drawn laterally outwards away from the mouthpiece and in a third position the straps are unstretched (i.e. in a resting position) once the cap has been rotated in an anti-clockwise direction fully exposing the mouthpiece for use.

In one embodiment there is provided an inhaler for dispensing doses of medicament, the inhaler comprising:
(a) a housing including a mouthpiece from which the medicament is dispensed
(b) and an inhaler accessory comprising:
  a jacket which attaches to the housing;
  a removable and replaceable cap for the mouthpiece
  and a plurality of elastomeric straps which connect the jacket to the cap;
wherein one end of each strap is pivotally secured to a jacket side wall and the other end of each strap is immovably secured to a corresponding cap side wall, and wherein each strap is partially stretched by less than 10% when the cap is engaged with the mouthpiece.

Definitions

It will be understood that particular embodiments described herein are shown by way of illustration and not as limitations of the invention. The principal features of this invention can be employed in various embodiments without departing from the scope of the invention. Those skilled in the art will recognise, or be able to ascertain using no more than routine study, numerous equivalents to the specific procedures described herein. Such equivalents are considered to be within the scope of this invention and are covered by the claims.

The term "snap-fit fixing" refers to male and female elements with a co-operating interlocking relationship, which are adapted to permanently engage with one another.

The term "click-fit arrangement" refers to male and female elements with a co-operating relationship, for example, projections in a co-operating relationship with grooves, but such arrangements are non-permanent.

The term "clip fixing" refers to an element or protrusion for holding an object in place. Unlike a snap-fit fixing, a clip fixing does not require a co-operating engaging male or female counterpart. In this instance the protrusion directly engages with the inhaler housing to ensure secure fixing.

The term "tensile force" refers to the stress, tension or pull exerted on a material, which results in the material stretching.

The term "elongation" refers to deformation, extension, lengthening or stretching caused by a tensile force. Elongation is expressed as the percentage of stretch over the original length.

The term "total % strap elongation" refers to the total increase in strap length compared to the original length of the strap expressed as a percentage.

The term "elasticity" refers to the ability of a material to stretch or elongate when tension is applied, and to recover to its original shape when the tension is released or removed.

FIGURES

The present invention is further described with reference to the drawings, in which.

LIST OF NUMERICAL REFERENCES USED IN THE FIGURES

| | |
|---|---|
| 1 | Jacket |
| 2 | Jacket upper collar |
| 3 | Jacket semi-circular base |
| 4a, 4b | Jacket side walls |
| 5a, 5b, 5c | Jacket snap-fit or clip protrusions |
| 6a, 6b | Jacket semi-circular flange |
| 7a, 7b | Jacket circular aperture |
| 8a, 8b | Strap |
| 9a, 9b | Strap engaging protrusion i.e. pivot pin |
| 10a, 10b | Pivot hinge assembly |
| 11a, 11b | Cap strap end |
| 12 | Cap |
| 13a, 13b | Cap side wall |
| 14a, 14b | Central expansion region |
| 15 | Central expansion region openings |
| 16a, 16b | Raised jacket section |
| 17a, 17b | Jacket aperture recess |
| 18 | Metered dose inhaler |
| 19 | Canister |
| 20 | Actuator housing |
| 21 | Mouthpiece |
| 22 | Pivot pin head portion |
| 23 | Pivot pin circular rod portion |
| 24 | Pivot pin oval rod portion |
| 25a, 25b | Jacket key-hole shaped aperture |
| 26 | Central expansion region cuts |

Figure 1A:
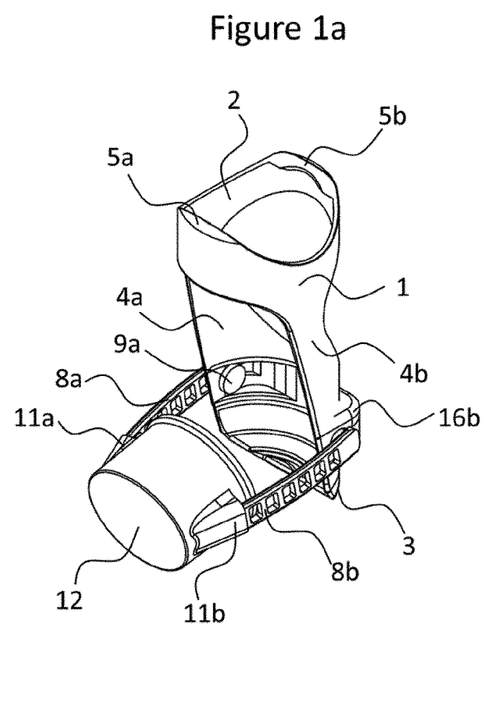
FIG. 1a shows a front view of a first inhaler jacket with cap attachment according to the invention.
Figure 1B:
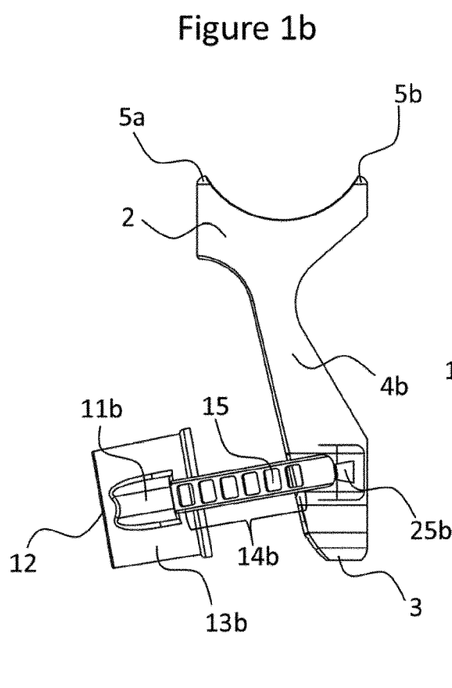
FIG. 1b shows a side view of a first inhaler jacket with cap attachment according to the invention.
Figure 1C:
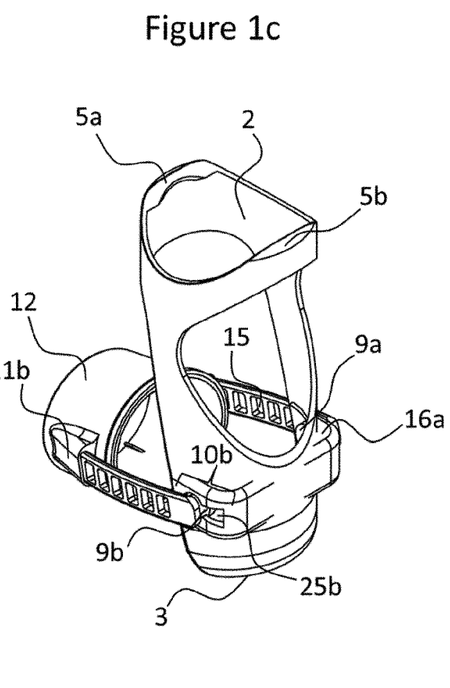
FIG. 1c shows a back view of a first inhaler jacket with cap attachment according to the invention.

FIGS. 1*a*, 1*b* and 1*c* are respectively side, front and back views showing a first inhaler jacket with cap attachment according to the invention.

The jacket 1 is configured to receive and permanently attach to an actuator housing (not shown) of a medical device. The jacket 1 comprises an upper collar 2; a semi-circular base 3 and a pair of side walls 4*a*, 4*b*, which extend vertically between and connect to the upper collar 2 and the semi-circular base 3. The jacket further includes two opposing openings, wherein each opening is surrounded by the upper collar 2, the base 3, and the pair of side walls 4*a*, 4*b*.

The upper collar 2 attaches to the top of the actuator housing (not shown). Attachment involves at least one snap-fit fixing or at least one clip fixing. This is achieved by the provision of protrusions 5*a*, 5*b*, which protrude inwardly from the inner surface of the upper collar 2. The upper collar 2 can have any suitable configuration. Depending on the shape of the actuator opening, the upper collar 2 may have an annular or non-annular configuration. The purpose of the upper collar 2 is to surround the external wall of the top of the actuator opening fixing the jacket 1 in place. Preferably the jacket is provided with an eyelet (not shown) which may be located near to the top of the jacket, more preferably on the outer surface of the upper collar 2.

Projecting downwards from the upper collar 2 towards the semi-circular base 3 are two side walls 4*a*, 4*b*. The lower end of each side wall is provided with a key-hole shaped receiving aperture 25*a*, 25*b* positioned on a raised section 16*a*, 16*b*.

The semi-circular base 3 is also provided with at least one snap-fit fixing or at least one clip fixing. Fixing is achieved by an inwardly protruding protrusion 5*c* from the inner surface of the semi-circular base 3, which engages with the base of the inhaler housing (not shown).

The jacket is attached to the cap by a pair of straps 8*a*, 8*b*. One end of each strap is pivotally attached to the jacket by engaging protrusions 9*a*, 9*b*, which are held captive by key-hole shaped receiving apertures 25*a*, 25*b* positioned centrally on raised sections 16*a*, 16*b* of the lower jacket side walls 4*a*, 4*b*. The engaging protrusions 9*a*, 9*b* are pivot pins with a flat circular head portion and an oval rod portion. This engaging/receiving arrangement, termed the pivot hinge assembly 10*a*, 10*b* ensures that each strap is securely attached to the jacket but remains freely rotatable.

The other end of each strap 11*a*, 11*b* is immovably secured to the cap 12 side walls 13*a*, 13*b*. Each strap is also provided with a central expansion region 14*a*, 14*b* having a plurality of substantially rectangular openings 15 that temporarily elongate during strap extension.

Figure 2A:
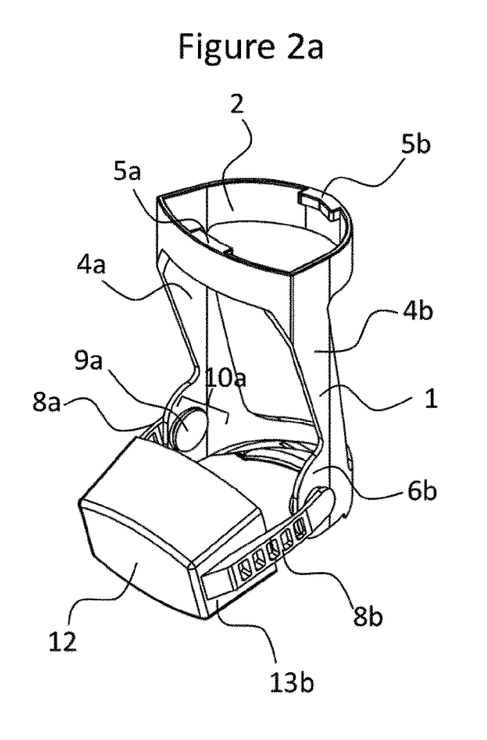
FIG. 2a shows a front view of an alternative inhaler jacket with cap attachment according to the invention.
Figure 2B:
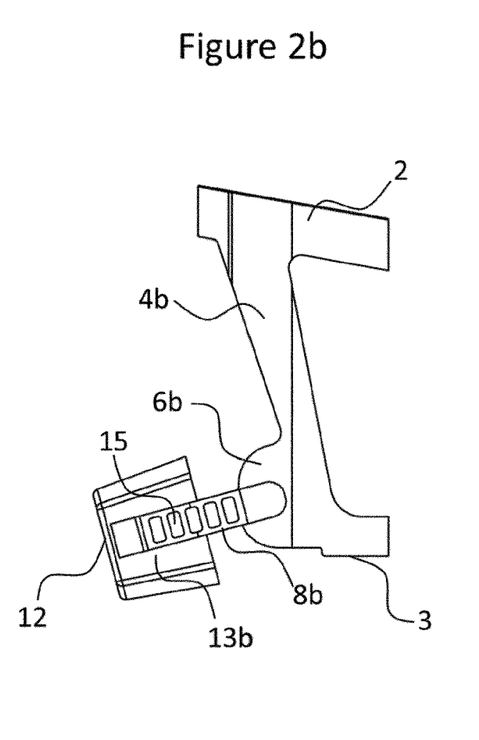
FIG. 2b shows a side view of an alternative inhaler jacket with cap attachment according to the invention.
Figure 2C:
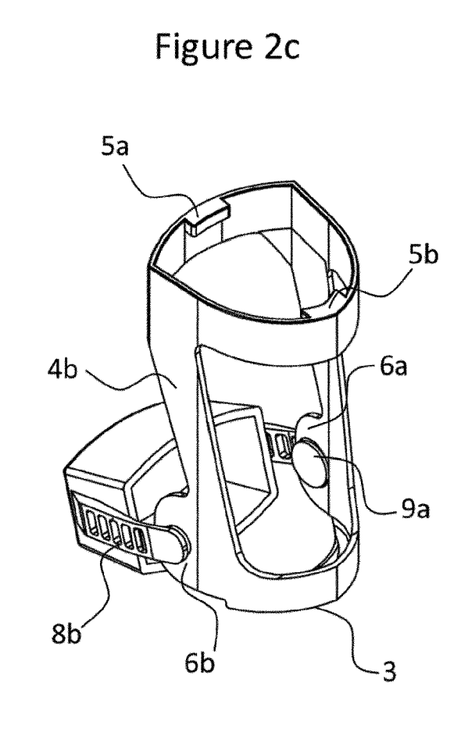
FIG. 2c shows a back view of an alternative inhaler jacket with cap attachment according to the invention.

FIGS. 2*a*, 2*b* and 2*c* are respectively side, front and back views showing an alternative inhaler jacket with cap attachment according to the invention. This alternative inhaler accessory corresponds to the first inhaler accessory supra in all aspects bar some of the structural features of the lower end of the jacket side walls 4*a*, 4*b* and the strap engaging protrusions 9*a*, 9*b*.

Here, the jacket 1 is also attached to the cap by a pair of straps 8*a*, 8*b*. One end of each strap is pivotally attached to the jacket by engaging protrusions 9*a*, 9*b*, which are held captive by circular receiving apertures 7*a*, 7*b* located on semi-circular flanges 6*a*, 6*b* of the lower jacket side walls 4*a*, 4*b*. The semi-circular flanges 6*a*, 6*b* can be considered an extension of the lower end of the jacket side walls 4*a*, 4*b*. The engaging protrusions 9*a*, 9*b* are pivot pins with a flat circular head portion 22 and a circular rod portion 23. This engaging/receiving arrangement, termed the pivot hinge assembly 10*a*, 10*b* ensures that each strap is securely attached to the jacket but remains freely rotatable.

Figure 3A:
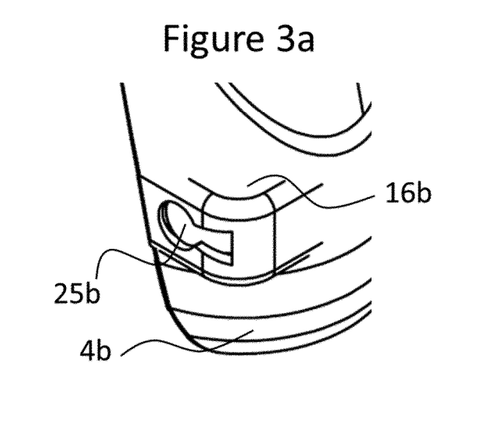
FIG. 3a shows a side view of a key-hole shaped receiving aperture of the first inhaler accessory hinge assembly according to the invention.
Figure 3B:
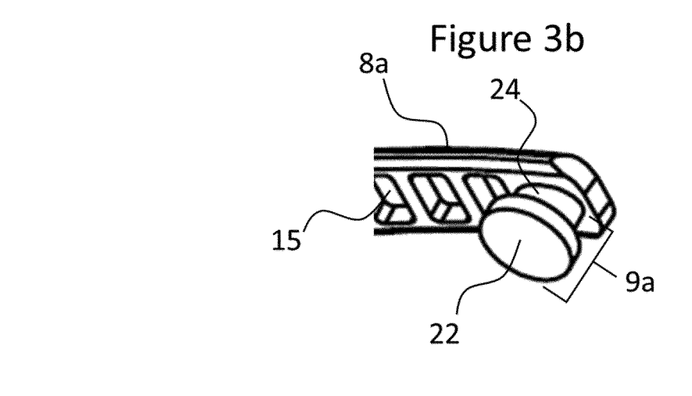
FIG. 3b shows a side view of a strap end with an integrally moulded pivot pin thereon of the first inhaler accessory hinge assembly according to the invention.
Figure 3C:
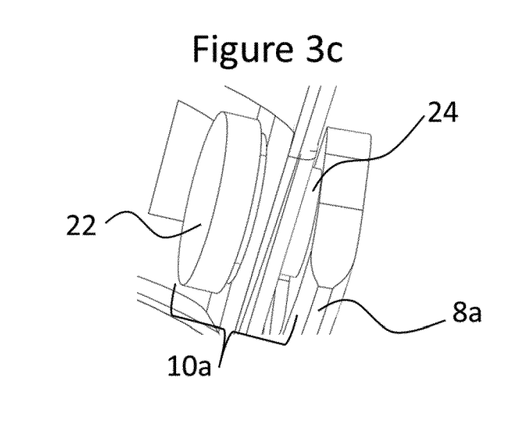
FIG. 3c shows a side view of an assembled hinge of the first inhaler accessory hinge assembly according to the invention.
Figure 3D:
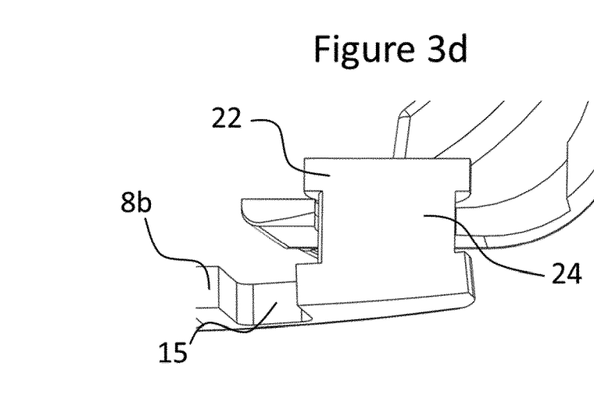
FIG. 3d shows a cross-sectional view of an assembled hinge of the first inhaler accessory hinge assembly according to the invention.

FIGS. 3*a* and 3*b* show side views of the two hinge components and FIGS. 3*c* and 3*d* show respective side and cross sectional view of an assembled pivot hinge 10*a* of the first inhaler accessory according to the invention. FIG. 3*a* shows a key-hole shaped receiving aperture 25*b* located on a raised section 16*b* of a lower jacket side wall 4*b*. FIG. 3*b* shows a strap end with an integrally moulded pivot pin 9*a* thereon. The pivot pin consists of a circular flat head portion 22, and an oval rod portion 24. The circular flat head portion 22 is generally enlarged having a larger diameter than the diameter of the circular section of the key-hole shaped receiving aperture 25*a*. The pivot pin 9*a* is integrally moulded to one end of the strap, specifically to the side of the strap facing the jacket. Strap insertion generally involves a transfer of the pivot pin 9*a* from the tapered end of the key-hole shaped receiving aperture 25*a* to the circular section by temporary deformation of the oval rod portion 24.

Figure 4A:
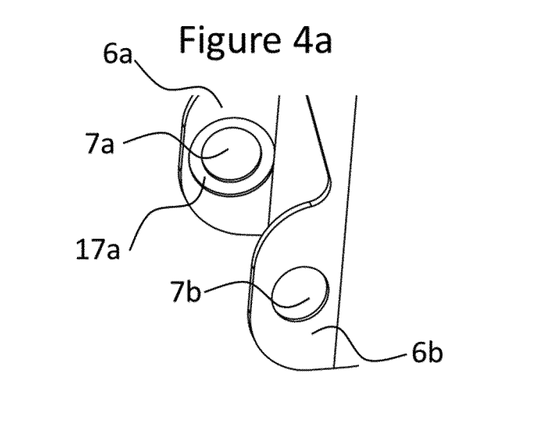
FIG. 4a shows a side view of a circular receiving aperture of an alternative inhaler accessory hinge assembly according to the invention.
Figure 4B:
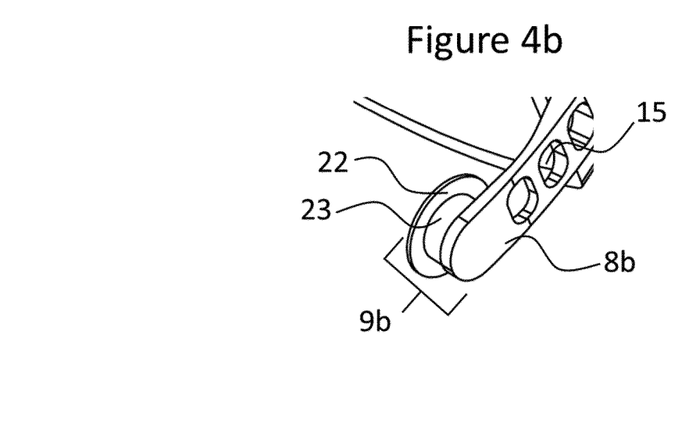
FIG. 4b shows a side view of a strap end with an integrally moulded pivot pin thereon of an alternative inhaler accessory hinge assembly according to the invention.
Figure 4C:
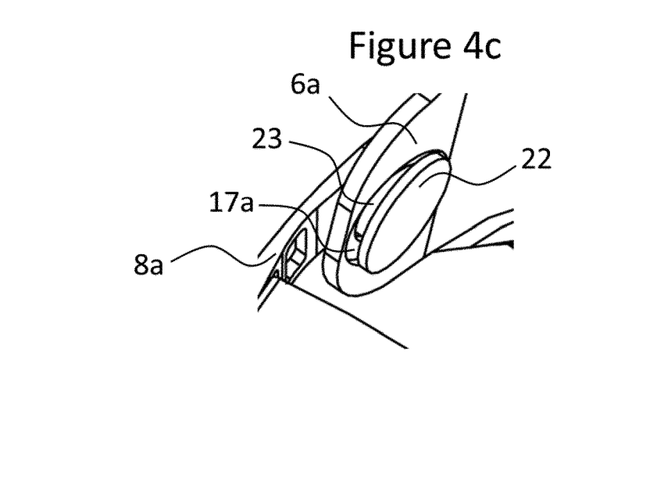
FIG. 4c shows a side view of an assembled hinge of an alternative inhaler accessory hinge assembly according to the invention.
Figure 4D:
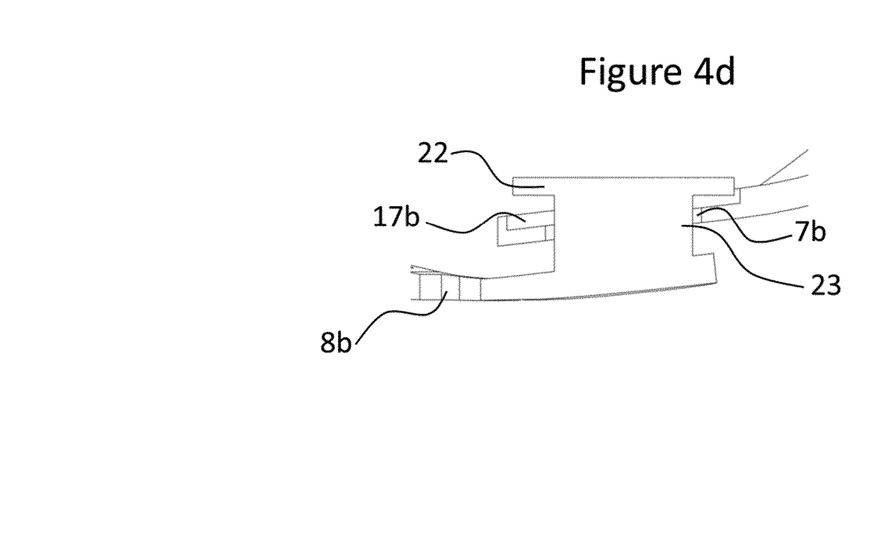
FIG. 4d shows a cross-sectional view of an assembled hinge of an alternative inhaler accessory hinge assembly according to the invention.

FIGS. 4*a* and 4*b* show side views of the two hinge components and FIGS. 4*c* and 4*d* show respective side and cross sectional view of an assembled pivot hinge 10*a* of an alternative inhaler accessory according to the invention. FIG. 4*a* shows a circular receiving aperture 7*a* located on a semi-circular flange 6*a*. The circular receiving aperture 7*a* is provided with a recess 17*a* to ensure that the flat circular head portion of the pivot pin fits flush with the inner surface of the jacket wall. FIG. 4*b* shows a strap end with an integrally moulded pivot pin 9*b* thereon. The pivot pin consist of a circular flat head portion 22 and a circular rod portion 23. The circular flat head portion 22 is generally enlarged having a larger diameter than the diameter of the circular receiving aperture 7b, retaining the pin within the circular receiving aperture. The pivot pin is integrally moulded to one end of the strap, specifically to the side of the strap facing the jacket.

Figure 5A:
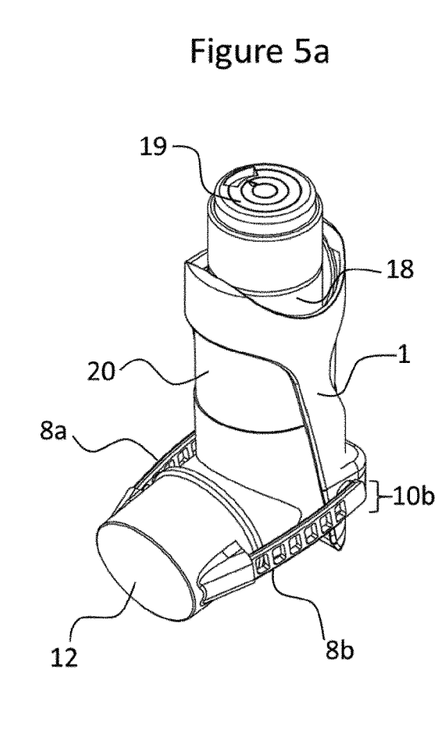
FIG. 5a shows a perspective view of an assembled inhaler, including the first inhaler jacket with cap attachment according to the invention, the cap being shown in a closed position engaging with the mouthpiece (first position).
Figure 5B:
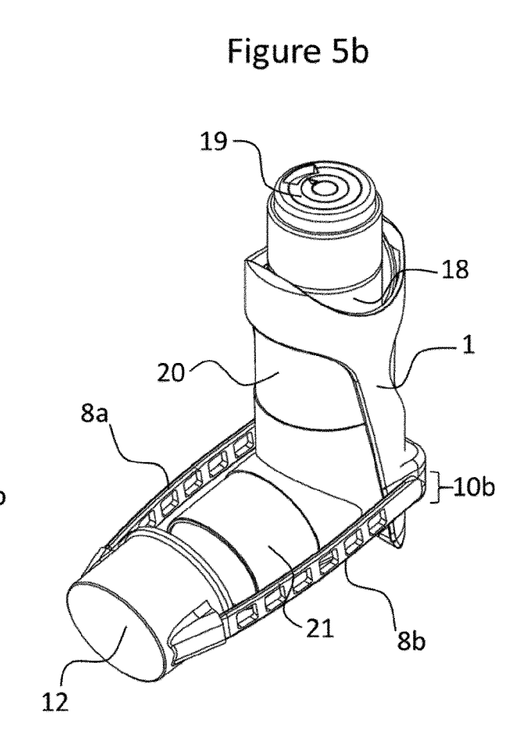
FIG. 5b shows a perspective view of an assembled inhaler, including the first inhaler jacket with cap attachment according to the invention, the cap being drawn laterally outwards away from the mouthpiece (second position).
Figure 5C:
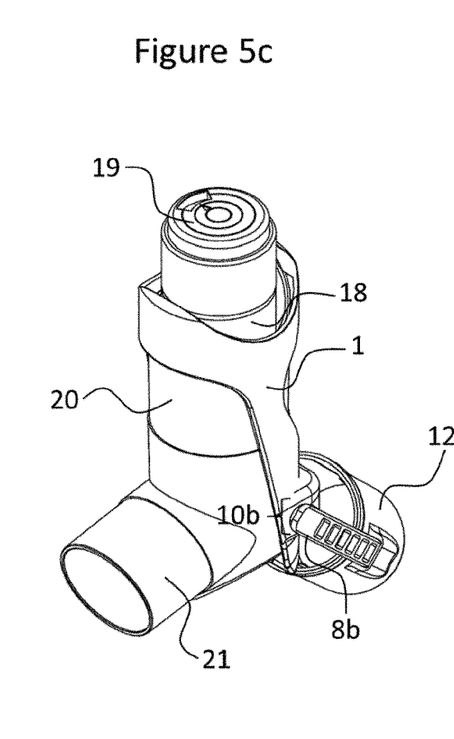
FIG. 5c shows a perspective view of an assembled inhaler, including the first inhaler jacket with cap attachment according to the invention, the cap being shown in a fully open position exposing the mouthpiece for use (third position).

FIGS. 5a, 5b and 5c show a perspective view of an assembled metered dose inhaler 18, including the first inhaler jacket 1 with cap attachment according to the invention in various cap positions. The inhaler 18 is illustrated as having a canister 19 of medication in place within the actuator housing 20. FIG. 5a shows the cap 12 in a closed or first position engaging with the mouthpiece 21. In this position the straps 8a, 8b are partially stretched. In order to move the cap 12 from this position to an open position ready for use as shown in FIG. 5c, it is necessary to pull the cap 12 away from the mouthpiece 21 so that the cap 12 extends beyond the axial extent of the mouthpiece 21 as shown in FIG. 5b. In this intermediate position (or second position) the straps 8a, 8b are stretched or fully stretched. The maximum extended length of each strap 8a, 8b must correspond to at least this stretched or fully stretched configuration. The cap 12 is then moved into an open position (or third position) fully exposing the mouthpiece 21 as shown in FIG. 5c, by moving the straps about their hinges 10a, 10b in an anti-clockwise direction. In this open position, when the user inhales, the straps 8a, 8b are unstretched.

In order to re-attach the cap 12, the user must move the straps 8a, 8b about their hinges 10a, 10b in a clockwise direction. The cap 12 is then pulled to stretch or fully stretch the straps 8a, 8b in order to axially align the cap with the mouthpiece 21. The cap 12 is then pushed towards the mouthpiece 21 until the mouthpiece 21 is fully engaged. The straps 8a, 8b then return to a partially stretched configuration.

Figure 6:
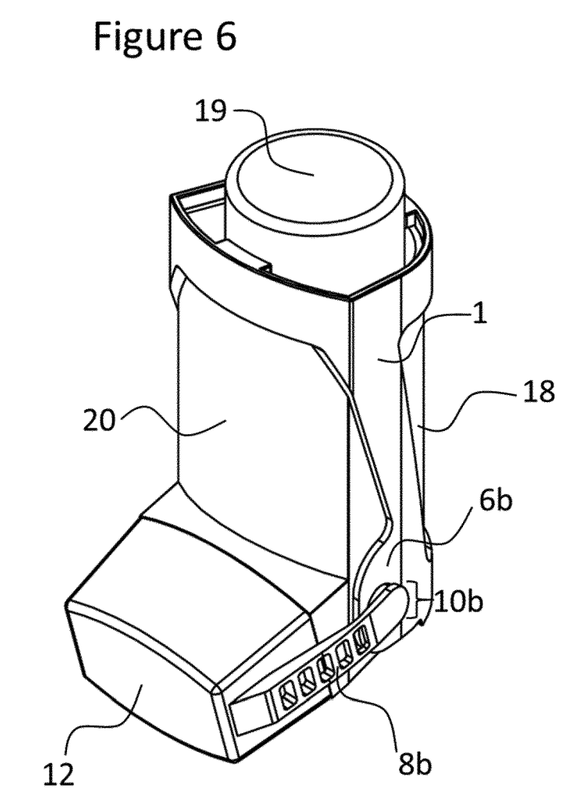
FIG. 6 shows a perspective view of an assembled inhaler, including an alternative inhaler jacket with cap attachment according to the invention, the cap being shown in a closed position engaging with the mouthpiece (first position).

FIG. 6, shows a perspective view of an assembled metered dose inhaler 18, including an alternative inhaler jacket with cap attachment according to the invention in the closed cap or first position. The process of cap removal and cap attachment will correspond in all aspects to the process described for the first inhaler with cap attachment (FIGS. 5a, 5b, 5c) and so will not be discussed here any further.

Figure 7A:
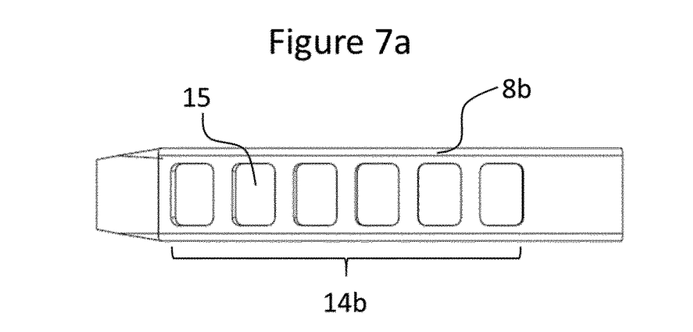
FIG. 7a shows a perspective view of a cap strap according to the invention, wherein the strap is in an unstretched, resting position.
Figure 7B:
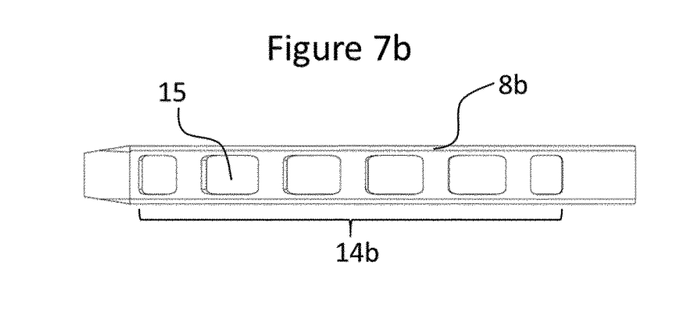
FIG. 7*b* shows a perspective view of a cap strap according to the invention, wherein the strap is in a stretched or fully stretched position.

FIGS. 7a and 7b show respectively a strap 8b of the present invention in two different configurations; the unstretched and stretched or fully stretched state. The strap 8b is provided with a central expansion region 14b which is flanked on one side by the end region that is immovably secured to a cap side wall 13b and on the other side by the end region that is pivotally secured to the corresponding jacket side wall 4b. Stretching or fully stretching the strap causes the plurality of rectangular openings 15 of the central expansion region 14b to temporarily change shape and elongate. The width of the rectangular openings 15 will increase and the height of the rectangular openings 15 will decrease.

Only upon removal of the applied stress will the strap return to an unstretched state and the rectangular openings revert back to their original shape.

Figure 8A:
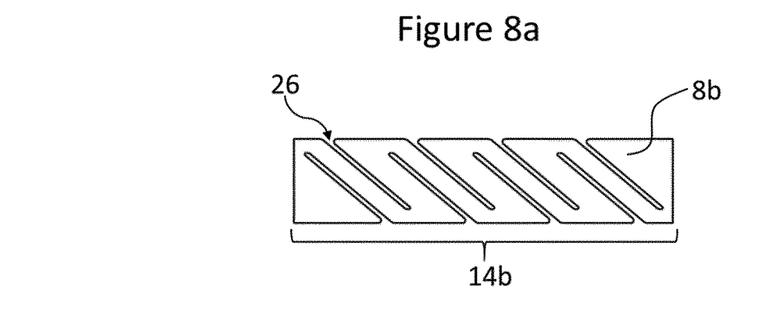
FIG. 8*a* shows a perspective view of an alternative cap strap according to the invention, wherein the strap is in an unstretched, resting position.
Figure 8B:
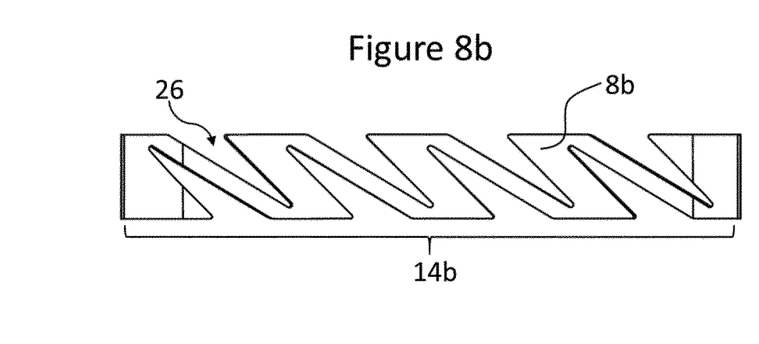
FIG. 8*b* shows a perspective view of an alternative cap strap according to the invention, wherein the strap is in a stretched or fully stretched position.

FIGS. 8a and 8b show respectively an alternative strap 8b of the present invention in two different configurations; the unstretched and stretched or fully stretched state. The strap 8b is provided with a central expansion region 14b which is flanked on one side by the end region that is immovably secured to a cap side wall 13b and on the other side by the end region that is pivotally secured to the corresponding jacket side wall 4b (not shown). Stretching or fully stretching the strap causes the plurality of alternating top and bottom cuts 26 to separate. Only upon removal of all the applied stress will the strap return to an unstretched state and the central expansion region 14b revert back to its original shape.

The invention claimed is:

1. An accessory for an inhaler, the accessory comprising:
   (a) a jacket configured to attach to a housing;
   (b) a cap for a mouthpiece;
   (c) and a pair of elastomeric straps which connects the jacket to the cap;
   wherein the jacket comprises an upper collar portion, a lower base portion, and a pair of side walls connecting to the upper collar portion and the lower base portion whereby two opposing openings are formed wherein each opening is surrounded by the upper collar portion, the lower base portion,
   and the pair of side walls, wherein the two opposing openings are not the same size; wherein the upper collar comprises an upper opening configured to receive the housing;
   wherein one end of each of the straps is secured to the jacket and the other end of each of the straps is secured to the cap; and
   wherein the pair of elastomeric straps is diametrically opposed.

2. The accessory according to claim 1, wherein each of the straps is partially stretched by less than 10% when the cap is engaged with the mouthpiece.

3. The accessory according to claim 1, wherein the jacket is permanently attached to the housing.

4. The accessory according to claim 1, wherein the jacket is made from a rigid plastics material.

5. The accessory according to claim 1, wherein the elastomeric straps are made from a thermoplastic elastomer or a liquid silicone rubber.

6. The accessory according to claim 1, wherein each strap is pivotally secured to the jacket side wall by a separate pivot hinge.

7. The accessory according to claim 6, wherein the pivot hinge assembly comprises a receiving member located on the jacket side wall and an engaging pivot member integrally moulded to the strap.

8. The accessory according to claim 1, wherein each strap is immovably secured to the cap.

9. An inhaler for dispensing doses of a medicament, the inhaler comprising:
   (a) a housing including a mouthpiece from which the medicament is dispensed and
   (b) an inhaler accessory comprising:
   (c) a jacket configured to attach to the housing;
   (d) a cap for the mouthpiece; and
   (e) a pair of elastomeric straps which connects the jacket to the cap;
   wherein the jacket comprises an upper collar portion, a lower base portion, and a pair of side walls connecting to the upper collar portion and the lower base portion whereby two opposing openings are formed wherein each opening is surrounded by the upper collar portion, the lower base portion,
   and the pair of side walls, where in the two opposing openings are not the same size; wherein the upper collar comprises an upper opening configured to receive the housing;
   wherein one end of each of the straps is secured to the jacket and the other end of each of the straps is secured to the cap; and wherein the pair of elastomeric straps is diametrically opposed.

10. The inhaler according to claim 9, wherein the inhaler is a pressurized metered dose inhaler.

11. The inhaler according to claim 9, wherein the cap is movable by a user between first, second and third positions and is configured to remain attached to the jacket in each position; in a first position the cap is arranged to engage with the mouthpiece; in a second position the cap is adapted to be drawn laterally outwards away from the mouthpiece and in a third position the cap is rotated by a user in an anti-clockwise direction fully exposing the mouthpiece for use.

12. The inhaler according to claim 11, wherein the straps in the third position are less stretched than in the first and second positions.

13. The inhaler according to claim 11, whereby, in the third position, the cap will have been rotated at least 70 degrees by the user about a horizontal axis of rotation.

* * * * *